United States Patent [19]
Fuxe

[11] 3,947,579
[45] Mar. 30, 1976

[54] METHOD AND COMPOSITION FOR POTENTIATING NEUROLEPTIC DRUGS

[75] Inventor: Kjell Fuxe, Sollentuna, Sweden

[73] Assignee: Nelson Research & Development Company, Irvine, Calif.

[22] Filed: June 3, 1974

[21] Appl. No.: 475,856

[52] U.S. Cl. ............... 424/267; 424/247; 424/262; 424/303; 424/319; 424/356
[51] Int. Cl.² ............... A61K 31/195; A61K 31/445
[58] Field of Search ........................... 424/267, 319

[56] References Cited
UNITED STATES PATENTS

| | | | |
|---|---|---|---|
| 3,471,548 | 10/1969 | Keberle | 424/309 |
| 3,505,451 | 4/1970 | Brunings | 424/244 |

*Primary Examiner*—Stanley J. Friedman
*Attorney, Agent, or Firm*—Martin Voet

[57] ABSTRACT

A method and composition for potentiating the effects of neuroleptic drugs by administering to a human having a disorder normally treatable with a neuroleptic drug, a neuroleptic drug in combination with a potentiating amount of an amino acid of the formula

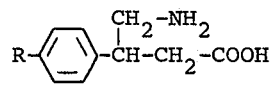

where R is fluorine, chlorine, bromine or trifluoromethyl and their salts.

8 Claims, No Drawings

METHOD AND COMPOSITION FOR POTENTIATING NEUROLEPTIC DRUGS

BACKGROUND OF THE INVENTION

BACKGROUND OF THE PRIOR ART

U.S. Pat. No. 3,471,548 describes compounds having the structural formula

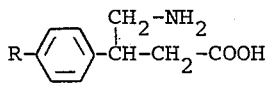

wherein R is chloro, bromo, fluoro or fluoromethyl. The compounds are known to cross the blood brain barrier and are known to have muscle relaxant properties and to be useful in the treatment in man of spasticity of spinal origin.

Neuroleptic drugs are used to treat schizophrenia. Examples of common neuroleptic drugs include phenothiazines such as chlorpromazine; butyrophenones such as haloperiodal and others such as pimocide and clozapine. Side effects of neuroleptic drugs include sedation and tardive dyskinesias. The latter side effect is particularly important because it results in involuntary muscle movements especially of the face and mouth which become irreversible. The onset of this side effect is directly related to the amounts of and length of time which a neuroleptic drug is used in treatment.

SUMMARY OF THE INVENTION

There has now been discovered a method and composition whereby the foregoing side effects of neuroleptic drugs can be decreased.

The present invention relates to a method for reducing the side effects of neuroleptic drugs comprising administering to a schizophrenic about 10 to about 50% of an otherwise effective amount of a neuroleptic drug together with a potentiating amount of a compound having the structural formula

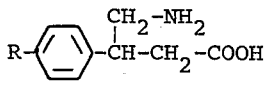

wherein R is halogen or trifluoromethyl and salts thereof.

The present invention further relates to a composition comprising about 10 to about 50% of an effective amount of a neuroleptic drug and a potentiating amount of a compound having the above described structural formula together with a suitable pharmaceutical carrier.

DETAILED DESCRIPTION OF THE INVENTION

Compounds having the foregoing structural formula such as, for example, β-(4-chlorophenyl)-gammaaminobutyric acid and pharmaceutically acceptable salts thereof and pharmaceutical compositions thereof and their manner of making is described in U.S. Pat. No. 3,471,548 and relevant portions thereof are hereby incorporated by this reference.

The amount of active potentiating compound which may be used in the present invention ranges from about 0.1 to about 50 mg/kg and preferably from about 0.1 to about 10 mg/kg and preferably about 0.1 to 1.5 mg/kg per day.

Neuroleptic drugs which may be used in the present invention include phenothiazine derivatives such as chlorpromazine, promozine, triflupromozine, acetophenazine, butaperozine, corphenazine, fluphenazine, perphenazine, prochlorperozine, thiopropazate, trifluoperazine, mepazine, mesoridazine, piperacetozine, theoridazine, chlorprothizine, thiothixine, benzoctamine, cidorepin, clomacran, clopenthixol, clothiapine, clothixamide, clozapine, dimeprozan, doxepin, lovapine, perlapine and pinovepin; rauwolfia derivatives including deserpidine, metaserpate, rescinnamine, reserpine, benzquinamide, oxypertine, tetrabenazine, indopine, indriline, methopholine, milipertine, molindone, solypertine, yohimbine and solertine; diphenylmethane derivatives including benactyzine, piperilate, azacyclonal, captodiamine, hydroxyzine, cyprolidol, hexandrol and pimizide; and butyrophenone derivatives including haloanisone, haloperidal, ozaperone, benperidal, carperone, droperidal, fluspirilene, meperone, penfluridol, pipamperone, seperidol, spiperone and trifluperidol. When used herein, the term "Neuroleptic drugs" refers to any neuroleptic drug such as, but not limited to, the foregoing neuroleptic drugs.

While applicant does not necessarily rely on the following theory of action as to why the potentiating compound potentiates the effects of neuroleptic drugs, applicant believes that known neuroleptic drugs act by blocking dopamine receptor activity in the brain. However, whenever the dopamine receptor activity is blocked, compensatory mechanisms are initiated by the central nervous system to restore normal dopamine receptor activity. The compensatory mechanisms may act by blocking normal gammaaminobutyric acid (GABA) activity of dopamine cell bodies, thus tending to increase dopamine levels. Applicant believes the potentiating compound acts by interfering with these compensatory mechanisms by increasing GABA activity and thereby potentiates the effect of neuroleptic drugs by maintaining the lower dopamine receptor activity initially caused by the neuroleptic drug. In this manner, the potentiating compound can be used to potentiate the effects of neuroleptic drugs. Furthermore, the side effect of tardive dyskinesia is minimized because this effect is due to presynaptic dopamine hyperactivity, which is antagonized by compounds such as β-(4-chlorophenyl)-gammaaminobutyric acid.

Thus, when used in combination with the foregoing neuroleptic drugs, the potentiating compound described herein allows the use of lower doses of neuroleptic drugs to obtain the same effect as obtained with higher doses of neuroleptic drug without the potentiating compound. That is, the dose of neuroleptics now given may be decreased by a factor of 2–10 times (about 10–50% of usual dose) when given in combination with an effective amount of the potentiating compound of the present invention.

The pharmaceutical compositions may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with an oil medium, for example arachis oil, liquid paraffin or olive oil.

Aqueous suspensions contain the active ingredients in admixture with excipients suitable for the manufacture of aqueous suspensions. Such excipients are suspending agents, for example sodium carboxymethyl cellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 10 mg and about 500 mg of the active ingredient of the formula stated above. A preferred dosage rate for oral administration is of the order of 1–1000 mg daily, optionally in divided doses.

From the foregoing formulation discussion, it is apparent that the compositions of this invention can be administered orally or parenterally. The term parenteral as used herein includes subcutaneous injection, intravenous, intramuscular, or intrasternal injection or infusion techniques.

This invention is further demonstrated by the following examples in which all parts are by weight.

EXAMPLE

The effect of $\beta$-(4-chlorophenyl)-gammaaminobutyric acid on the pimozide-induced increase in dopamine fluorescence disappearance from the neostriatum and subcortical limbic areas after treatment with $\alpha$-methyl tyrosine methyl ester $\alpha$-methyl tyrosine methyl ester (H 44/68), an inhibitor of dopamine synthesis, was given i.p. in a dose of 250 mg/kg 4 hrs before killing. $\beta$-(4-chlorophenyl)-gammaaminobutyric acid (Lioresal) was given i.p. in a dose of 10, 20 or 25 mg/kg 15 minutes before H 44/68. Pimozide was given i.p. in a dose of 1 mg/kg 2 hours before H 44/68, and haloperidol in a dose of 5 mg/kg 1 hour before H 44/68. The dopamine levels were determined by measuring histochemical fluorescence. The fluorescence intensity reflects the amount of dopamine present. The fluorescence intensity was semi-quantitatively estimated on coded slides. 3 = strong; 2 = moderate; 1 = weak; ½ = very weak. Number of animals is shown within parenthesis. The table below tabulates the data obtained.

Table

| Treatment | Fluorescence intensity | |
|---|---|---|
| | Neostriatum | Limbic forebrain |
| No drug treatment | 3(4) | 3(4) |
| H 44/68 | 0.5(1)  1(2)  1.5(2) | 0.5(2)  1(2)  1.5(1) |
| Pimozide + H 44/68 | 0(4)  0.5(1)$^a$ | 0(4)  0.5(1)$^d$ |
| Pimozide + Lioresal (20) + H 44/68 | 1.5(2)  2(2)$^b$ | 1.5(1)  2(3)$^e$ |
| Pimozide + Lioresal (10) + H 44/68 | 1(2)  1.5(3)$^c$ | 1(1)  1.5(3)  2(1)$^f$ |
| Haloperidol + H 44/68 | 0.5(1)  1(3) | 0.5(2)  1(2)$^g$ |
| Haloperidol + Lioresal (10) + H 44/68 | 1(1)  1.5(2)  2(1) | 2(2)  2.5(2)$^h$ |
| Lioresal (25) + H 44/68 | 1(1)  1.5(3) | 1(1)  1.5(1)  2(2) |

Table-continued

| Treatment | Fluorescence intensity | |
|---|---|---|
| | Neostriatum | Limbic forebrain |
| Lioresal (10) + H 44/68 | 1.5(2)  2(1) | 1.5(1)  2(1)  2.5(1) |

Statistical significance according to Tukey's Quick test:
a–b: $p<0.05$    d–e: $p<0.05$    g–h: $p<0.05$
a–c: $p<0.01$    d–f: $p<0.01$ Dopamine neuron nerve endings can be made to fluoresce strongly as a result of the presence of stored dopamine. These stores of dopamine are not static; there is a continual release, reuptake, degradation and de novo synthesis at the nerve ending.

α-methyl tyrosine methyl ester is an inhibitor of dopamine synthesis. Fluorescence microscopy shows that α-methyl tyrosine methyl ester depletes dopamine stores. Therefore, α-methyl tyrosine methyl ester may be used to determine dopamine turnover in the nerve endings since the higher the turnover is the higher the rate of DA depletion will be.

When dopamine receptors are blocked by drugs such as pimozide and haloperidol, the dynamic state of dopamine at and in the nerve endings increase. This appears as an increased disappearance of fluorescence after H 44/68. This increase results from a compensatory response to the decreased stimulation of the nerve cells normally receiving the dopamine stimulation.

The foregoing EXAMPLE shows that the compensatory increase in dynamic state of dopamine at the nerve endings normally induced by drugs such as pimozide and haloperidol is the result of the dopaminergic cells becoming hyperactive. The hyperactivity is antagonized by β-(4-chlorophenyl-gammaaminobutyric acid. Thus, as seen from the foregoing table, the increased disappearance (i.e. decrease in amount) of dopamine fluorescence from the neostriatum and especially the limbic forebrain seen after introduction of pimozide and haloperidol is significantly reduced by pretreatment with β-(4-chlorophenyl)-gammaaminobutyric acid.

I claim:

1. A method for potentiating the neuroleptic activity of butyrophenone derivatives having neuroleptic activity comprising administering to a schizophrenic about 10 to about 50 percent of a conventional dosage amount of a butyrophenone derivative having neuroleptic activity and an amount equal to about 0.1 to about 50 mg/kg of a compound, or a pharmaceutically acceptable salt thereof, having the structural formula

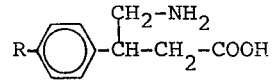

wherein R is selected from the group consisting of fluorine, chlorine, bromine and trifluoromethyl.

2. The method of claim 1 wherein R is chlorine.

3. The method of claim 1 wherein the butyrophenone derivative is selected from the group consisting of haloperidol and trifluperidol.

4. A method for potentiating the neuroleptic activity of butyrophenone derivatives comprising administering to a schizophrenic about 10 to about 50 percent of a conventional dosage amount of a butyrophenone derivative selected from the group consisting of haloperidol and trifluperidol and an amount equal to about 0.1 to about 10 mg/kg of β-(4-chlorophenyl)-gamma-aminobutyric acid or a pharmaceutically acceptable salt thereof.

5. A composition in unit dosage form comprising about 10 to about 50 percent of a conventional dosage amount of a butyrophenone derivative having neuroleptic activity and an amount equal to about 0.1 to about 50 mg/kg of a compound or a pharmaceutically acceptable salt thereof having the structural formula

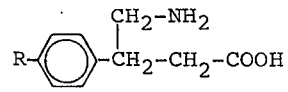

wherein R is selected from the group consisting of fluorine, chlorine, bromine and trifluoromethyl.

6. The composition of claim 5 wherein R is chlorine.

7. The composition of claim 5 wherein the butyrophenone derivative is selected from the group consisting of haloperidol and trifluperidol.

8. A composition in unit dosage form comprising about 10 to about 50 percent of a conventional dosage amount of a butyrophenone derivative selected from the group consisting of haloperidol and trifluperidol and an amount equal to about 0.1 to about 10 mg/kg of β-(4-chlorophenyl)-gammaaminobutyric acid or a pharmaceutically acceptable salt thereof.

* * * * *